United States Patent
Liao et al.

(10) Patent No.: US 8,986,394 B2
(45) Date of Patent: Mar. 24, 2015

(54) ARTIFICIAL DURA BIOMEDICAL DEVICE AND BRAIN SURGERY METHOD UTILIZING THE SAME

(75) Inventors: Chun-Jen Liao, Taipei (TW); Sheng-Hong Tseng, Taipei (TW); Huang-Chien Liang, Hsinchu (TW); Chun-Hung Chen, Hsinchu County (TW); Yi-Chun Su, Taoyuang County (TW)

(73) Assignees: Industrial Technology Research Institute, Hsinchu (TW); National Taiwan University Hospital, Taipei (TW)

( * ) Notice: Subject to any disclaimer, the term of this patent is extended or adjusted under 35 U.S.C. 154(b) by 152 days.

(21) Appl. No.: 13/458,903

(22) Filed: Apr. 27, 2012

(65) Prior Publication Data
US 2012/0215322 A1   Aug. 23, 2012

Related U.S. Application Data

(62) Division of application No. 12/650,398, filed on Dec. 30, 2009, now abandoned.

(60) Provisional application No. 61/141,610, filed on Dec. 30, 2008.

(51) Int. Cl.
*A61F 2/02* (2006.01)
*A61F 2/28* (2006.01)
*A61L 27/36* (2006.01)
*A61B 17/68* (2006.01)
*A61F 2/30* (2006.01)

(52) U.S. Cl.
CPC ............. *A61F 2/2875* (2013.01); *A61F 2/2846* (2013.01); *A61F 2002/285* (2013.01); *A61L 27/3675* (2013.01); *A61B 17/688* (2013.01); *A61F 2/30907* (2013.01); *A61F 2002/30433* (2013.01); *A61F 2002/30448* (2013.01); *A61F 2002/30462* (2013.01); *A61F 2220/0041* (2013.01); *A61F 2220/005* (2013.01); *A61F 2220/0075* (2013.01)
USPC ........................................................ 623/23.72

(58) Field of Classification Search
CPC ............ A61F 2/2846; A61F 2002/285; A61F 2/0063; A61L 27/3675; A61B 17/688
USPC ................. 623/23.72–23.76, 17.19; 606/151; 424/423–426; 128/898
See application file for complete search history.

(56) References Cited

U.S. PATENT DOCUMENTS 3,863,345 A   2/1975   Malmin
4,400,833 A   8/1983   Kurland
(Continued)

FOREIGN PATENT DOCUMENTS

EP   1537883 B1   4/2008

OTHER PUBLICATIONS

STIC search results, search performed Jan. 13, 2015, 18 pages.*

*Primary Examiner* — Gregory Anderson
*Assistant Examiner* — Christopher L Templeton

(57) ABSTRACT

An artificial dura biomedical device and a brain surgery method utilizing the same are disclosed. The steps includes: fixing an artificial dura to a partial skull; and fixing the partial skull with the artificial dura to a cut hole of a whole skull. The artificial dura biomedical device includes an artificial dura and a connecting element. The connecting element fixes the partial skull with the artificial dura.

12 Claims, 15 Drawing Sheets

(56) References Cited

U.S. PATENT DOCUMENTS

| | | | |
|---|---|---|---|
| 5,503,164 A | 4/1996 | Friedman | |
| 6,350,284 B1 | 2/2002 | Tormala et al. | |
| 7,833,253 B2 * | 11/2010 | Ralph et al. | 606/283 |
| 8,241,336 B2 * | 8/2012 | Ralph et al. | 606/281 |
| 2003/0040760 A1 | 2/2003 | Hnojewyj et al. | |
| 2007/0173844 A1 | 7/2007 | Ralph et al. | |
| 2007/0270974 A1 | 11/2007 | Aeschilimann et al. | |
| 2008/0027442 A1 * | 1/2008 | Blue | 606/72 |
| 2009/0076617 A1 * | 3/2009 | Ralph et al. | 623/17.19 |
| 2009/0259263 A1 * | 10/2009 | Steger et al. | 606/86 R |
| 2010/0094428 A1 * | 4/2010 | Ralph et al. | 623/17.19 |

* cited by examiner

ARTIFICIAL DURA BIOMEDICAL DEVICE AND BRAIN SURGERY METHOD UTILIZING THE SAME

CROSS REFERENCE TO RELATED APPLICATION

This application claims the benefit of U.S. Provisional Application No. 61/141,610, filed on Dec. 30, 2008, the entirety of which is incorporated by reference herein.

This application is a Divisional of abandoned U.S. patent application Ser. No. 12/650,398, filed Dec. 30, 2009 and entitled "Artificial dura biomedical device and brain surgery method utilizing the same".

BACKGROUND OF THE INVENTION

1. Field of the Invention

The present invention relates to an artificial dura biomedical device and a brain surgery method utilizing the same.

2. Description of the Related Art

During cerebral neurosurgery, a skull must be sawed and a dura must be broken. After finishing the cerebral neurosurgery, a surgeon uses dura substitutes to repair the broken dura. Clinically, the dura substitutes may be made of natural and synthetic materials, for example autografts, allografts, xenografts, absorbable or unabsorbable polymers. The dura substitutes help to prevent infection, bad tissue response, leakage of cerebrospinal fluid, and cerebral tissue adhesion. Further, the dura substitutes promote tissue regeneration of dura mater.

The dura repairing method comprises suture and non-suture methods. The suture methods are applied to the dura made of autografts, allografts, xenografts, and unabsorbable polymers (for example Neuro-Patch). Clinically, common problems include a long surgery procedure and an inconvenient operation so that surgery risk increases. To solve clinical requirements of dura repair, non-suture dura, for example DuraGen (Integra), is provided for a shorter surgery procedure and a more convenient operation so that surgery risk may decrease. Thus, non-suture dura is usually used.

The most frequent and convenient artificial dura used is DuraGen, made of collagen. Surgery method steps utilizing DuraGen only comprise cutting the DuraGen to be bigger than the broken dura and covering the cut DuraGen on the broken dura. However, non-suture dura has bad fixity so that the dura easily moves and cerebrospinal fluid leaks.

BRIEF SUMMARY OF THE INVENTION

The invention provides an artificial dura biomedical device. The artificial dura biomedical device is combined with a partial skull cut from a whole skull. The artificial dura biomedical device comprises an artificial dura and a connecting element. The connecting element fixes the partial skull with the artificial dura.

Note that the partial skull comprises a side surface, the artificial dura covers the partial skull and the connecting element fixes the artificial dura on the side surface.

Note that the connecting element comprises a binder, a screw, a hook, glue, or a nail.

Note that the partial skull comprises an upper surface, the artificial dura covers the partial skull and the connecting element fixes the artificial dura on the upper surface.

Note that the connecting element comprises a screw, a hook, a rivet, glue, or a nail.

Note that the partial skull comprises a plurality of holes, and the artificial dura passes through the holes to cover the partial skull and is fixed by the connecting element on the upper surface.

Note that the connecting element comprises a suture.

Note that the connecting element is installed between the partial skull and the artificial dura.

Note that the connecting element comprises two hook portions respectively inserted into the partial skull and the artificial dura.

Note that the connecting element comprises a base, a first engaging portion and a second engaging portion, the first engaging portion and the second engaging portion are installed at two opposite surfaces of the base, the first engaging portion is inserted into the partial skull, and the second engaging portion is inserted into the artificial dura.

Note that the connecting element comprises glue.

Note that the connecting element comprises a plurality of protrusions and grooves, the protrusions are installed on the artificial dura, the grooves are installed on the partial skull, and the protrusions are engaged with the grooves.

Note that the artificial dura biomedical device further comprises a plurality of pads and a ring, the pads are installed on the ring, the ring binds the artificial dura and the partial skull, and the pads are installed between the connecting element and the artificial dura for increasing friction.

The invention provides another artificial dura biomedical device. The artificial dura biomedical device is combined with a partial skull cut from a whole skull. The artificial dura biomedical device comprises an artificial dura. The artificial dura and the partial skull respectively comprise a plurality of protrusions and grooves, and the protrusions are engaged with the grooves for fixing the partial skull to the artificial dura.

Note that the protrusions and grooves are wedge shaped.

Note that the artificial dura is liquid at an initial state, and then the liquid artificial dura transforms into a colloidal or solid artificial dura.

The invention provides a brain surgery method utilizing an artificial dura biomedical device. The steps comprises fixing an artificial dura to a partial skull via a connecting member; and fixing the partial skull with the artificial dura to a cut hole of a whole skull.

Note that the steps further comprise cutting a partial skull from a whole skull.

Note that the steps further comprise drilling a hole on the partial skull.

Note that the steps further comprise making the artificial dura pass through the hole to cover the partial skull.

Note that step of fixing an artificial dura to the partial skull comprises fixing an artificial dura to the partial skull via a connecting member.

Note that the connecting element comprises a screw, a hook, a rivet, glue, a suture, or a nail.

Note that the step of fixing an artificial dura to the partial skull comprises fixing an artificial dura to the partial skull via a plurality of protrusions made of a liquid artificial dura engaging with a plurality of grooves of the partial skull.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
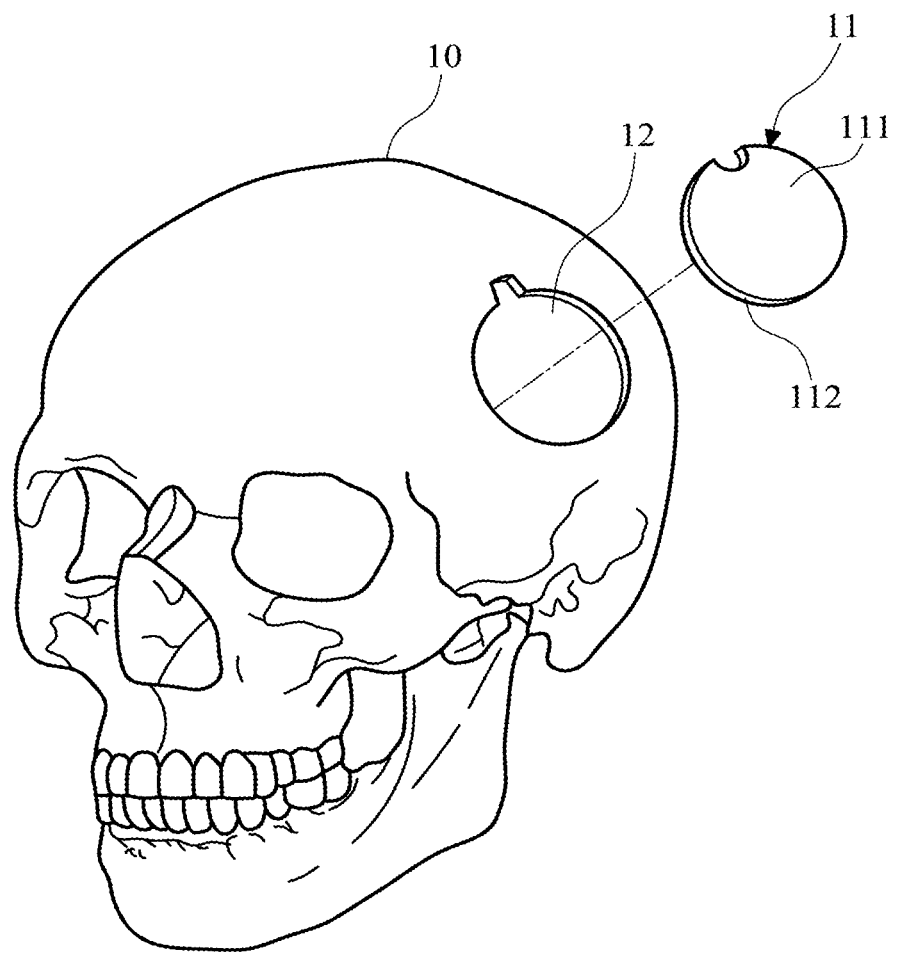
FIG. 1 is a schematic view showing a partial skull cut from a whole skull.
Figure 2:
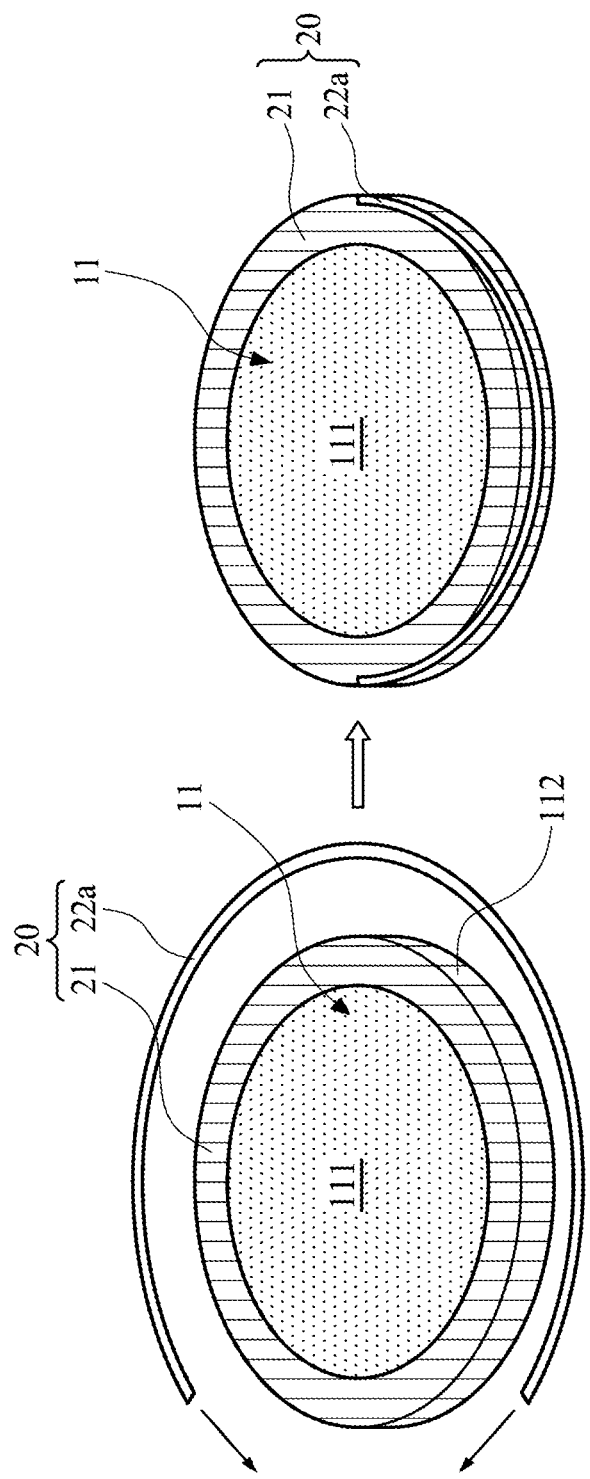
FIG. 2 is a schematic view showing a partial skull combined with an artificial dura biomedical device of an embodiment of the invention.
Figure 3:
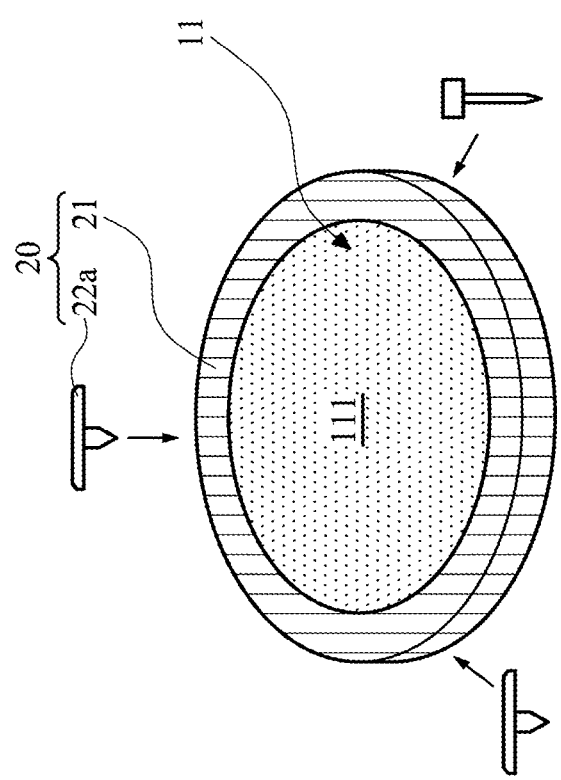
FIG. 3 is a schematic view showing a partial skull combined with an artificial dura biomedical device of another embodiment of the invention.
Figure 4:
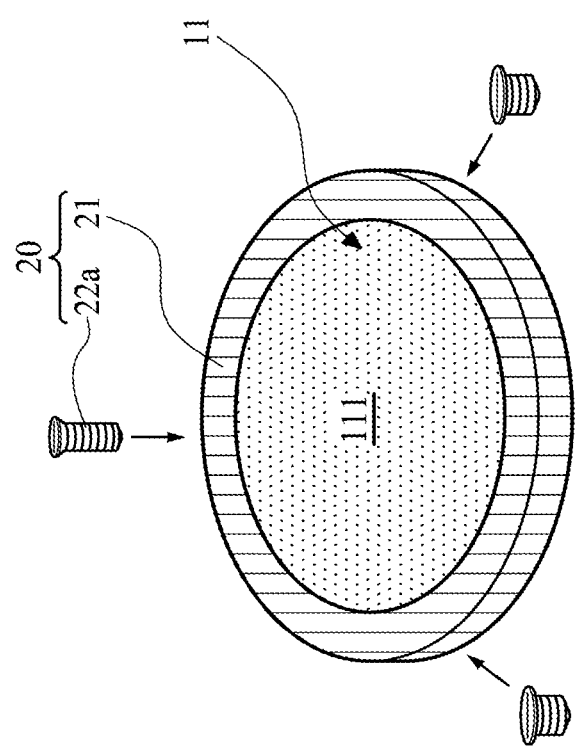
FIG. 4 is a schematic view showing a partial skull combined with an artificial dura biomedical device of another embodiment of the invention.
Figure 5:
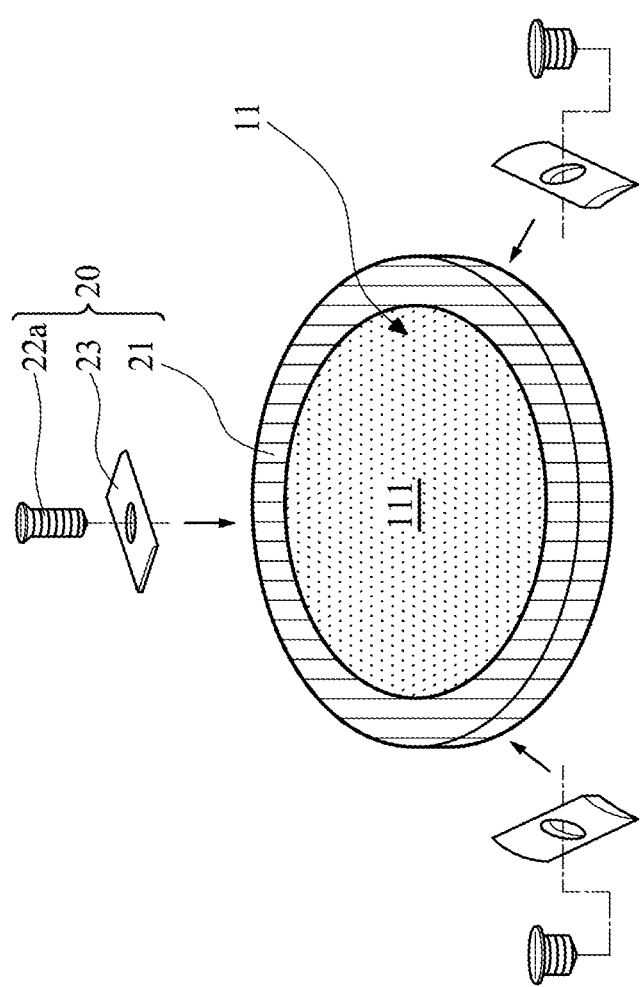
FIG. 5 is a schematic view showing a partial skull combined with an artificial dura biomedical device of another embodiment of the invention.
Figure 6:
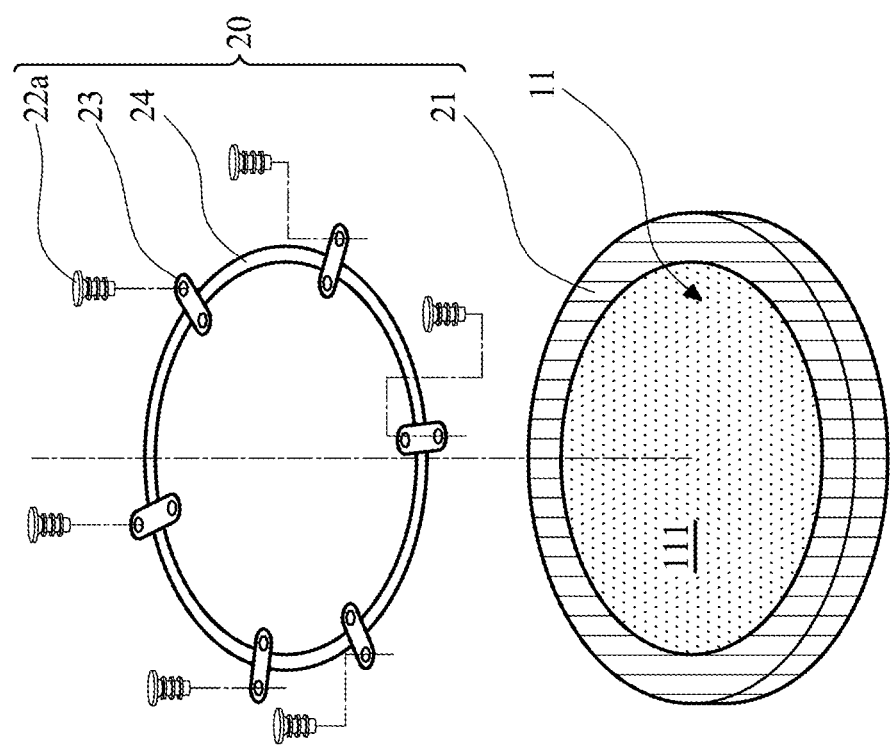
FIG. 6 is a schematic view showing a partial skull combined with an artificial dura biomedical device of another embodiment of the invention.

FIG. 1 is a schematic view showing a partial skull cut from a whole skull. FIG. 2 is a schematic view showing a partial skull combined with an artificial dura biomedical device of an embodiment of the invention. FIG. 3 is a schematic view showing a partial skull combined with an artificial dura biomedical device of another embodiment of the invention. FIG. 4 is a schematic view showing a partial skull combined with an artificial dura biomedical device of another embodiment of the invention. FIG. 5 is a schematic view showing a partial skull combined with an artificial dura biomedical device of another embodiment of the invention. FIG. 6 is a schematic view showing a partial skull combined with an artificial dura biomedical device of another embodiment of the invention.

Referring to FIGS. 1 and 2, during cerebral neurosurgery, a doctor cuts a partial skull 11 from a whole skull 10 and a dura under the whole skull 10 is broken. At this time, a cut hole is formed on the whole skull. After a doctor repairs the cerebral nerve, the broken dura must be repair and then the partial skull 11 is put to cover the cut hole 12. Thus, the artificial dura biomedical device of the invention is provided. The artificial dura biomedical device 20 comprises an artificial dura 21 and a connecting element 22*a*. The connecting element 22*a* fixes the partial skull 11 with the artificial dura 21. The partial skull 11 comprises an upper surface 111 and a side surface 112. Referring to FIG. 2, the artificial dura 21 of this embodiment covers the partial skull 11 and the connecting element 22*a* fixes the artificial dura 21 on the side surface 112. In this embodiment, the connecting element 22*a* is a binder for binding the artificial dura 21 and the partial skull 11. The connecting element 22*a* further comprises a screw, a hook, glue or a nail (not shown), and is not limited to the disclosed embodiment.

Referring to FIGS. 3 and 4, the structures of FIGS. 3 and 4 are approximately similar to that of FIG. 2 and like elements are omitted for brevity. The main difference is that the connecting element 22*a* fixes the artificial dura 21 on the upper surface 111. In the embodiments of FIGS. 3 and 4, the connecting element 22*a* comprises a screw, a hook, a rivet, glue, or a nail, and is not limited to the disclosed embodiment.

Referring to FIG. 5, the structures of FIG. 5 is approximately similar to that of FIG. 3, and like elements are omitted for brevity. The main difference is that the artificial dura biomedical device 20 further comprises a pad 23. The pad 23 is installed between the connecting element 22*a* and the artificial dura 21 for increasing friction.

Referring to FIG. 6, the structures of FIG. 5 is approximately similar to that of FIG. 3 and like elements are omitted for brevity. The main difference is that the artificial dura biomedical device 20 further comprises a plurality of pads 23 and a ring 24. The pads 23 are installed on the ring 24. The ring 24 binds the artificial dura 21 and the partial skull 11 and then the connecting element 22*a* passes through the pad 23 for fixing the artificial dura 21 to the partial skull 11. The pads 23 are installed between the connecting element 22*a* and the artificial dura 21 for increasing friction.

Figure 7:
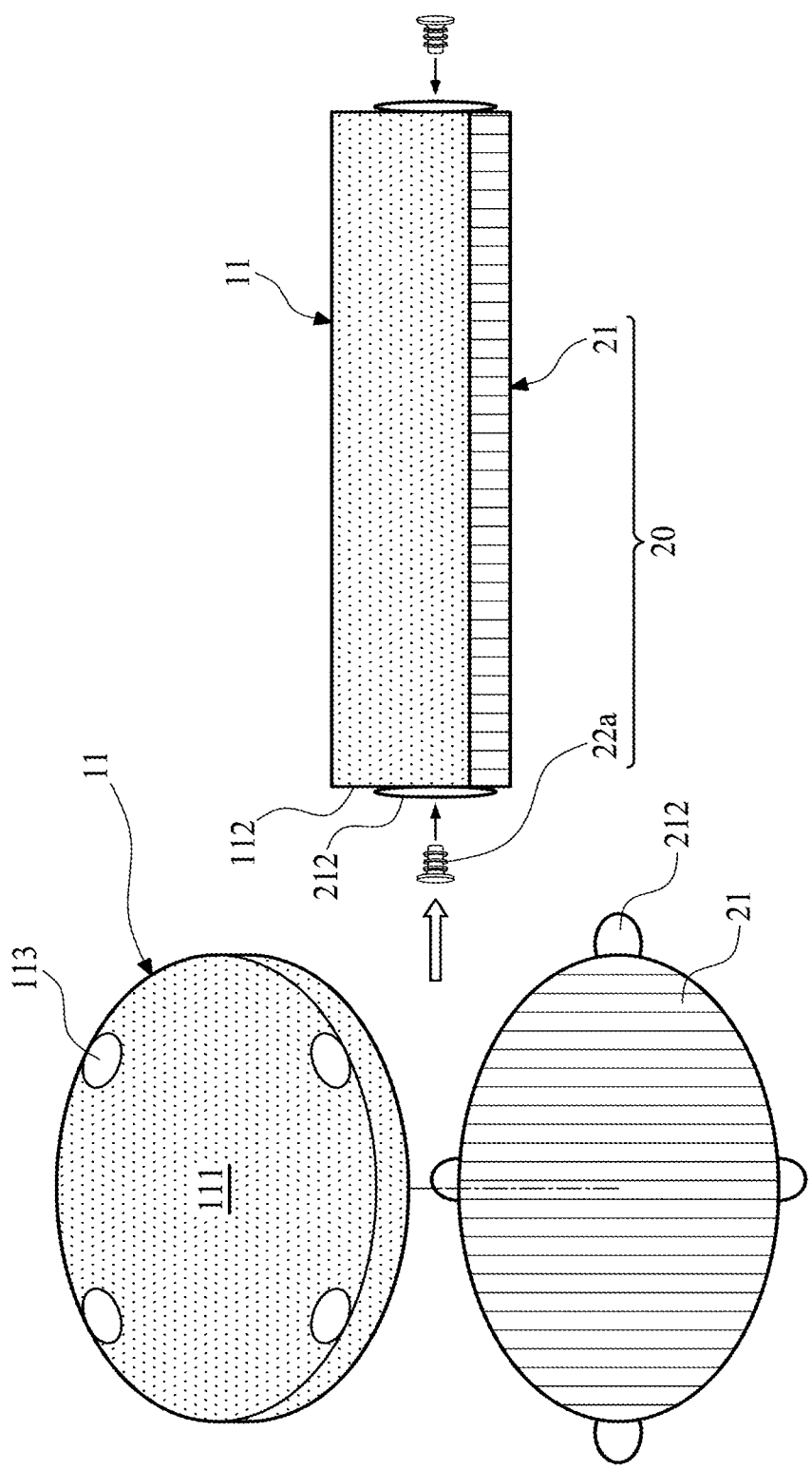
FIG. 7 is a schematic view showing a partial skull combined with an artificial dura biomedical device of an embodiment of the invention.
Figure 8:
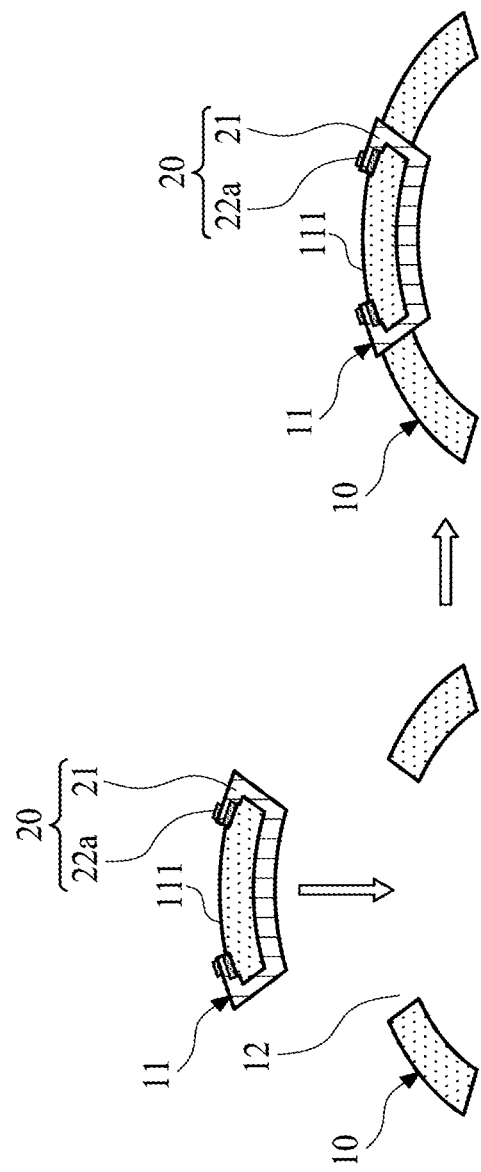
FIG. 8 is a schematic view showing a partial skull combined with an artificial dura biomedical device of another embodiment of the invention.

FIG. 7 is a schematic view showing a partial skull combined with an artificial dura biomedical device of an embodiment of the invention. FIG. 8 is a schematic view showing that a partial skull combined with an artificial dura biomedical device of another embodiment of the invention is combined with a whole skull.

Referring to FIG. 7, the artificial dura biomedical device 20 comprises an artificial dura 21 and a connecting element 22*a*. The partial skull 11 further comprises a plurality of holes 113 for a doctor to easily take the partial skull 11 from the whole skull 10 (shown in FIG. 1). The artificial dura 21 comprises four extending parts 212. The artificial dura 21 covers the partial skull 11 and is fixed by the connecting element 22*a* and the extending parts 212 on the side surface 112. In this embodiment, the connecting element 22*a* is a screw. The connecting element 22*a* further comprises glue (not shown), and is not limited to the disclosed embodiment.

Referring to FIG. 8, the artificial dura biomedical device 20 comprises an artificial dura 21 and a connecting element 22*a*. The artificial dura 21 covers the partial skull 11 and is fixed by the connecting element 22*a* on the upper surface 111 of the partial skull 11. In this embodiment, the connecting element 22*a* is a hook. The connecting element 22*a* further comprises glue (not shown), and is not limited to the disclosed embodiment. After the partial skull 11 is combined with the artificial dura 21, the partial skull 11 and the artificial dura 21 are put in and fills the cut hole 12 of the whole skull (referring to FIG. 1).

Figure 9:
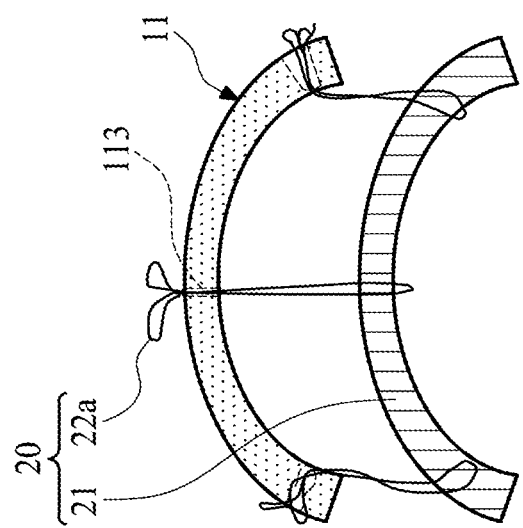
FIG. 9 is a schematic view showing a partial skull combined with an artificial dura biomedical device of another embodiment of the invention.

FIG. 9 is a schematic view showing a partial skull combined with an artificial dura biomedical device of another embodiment of the invention. Referring to FIG. 9, the partial skull 11 further comprises a plurality of holes 113. The connecting element 22a comprises a suture. The suture hangs the artificial dura 21. Then, the suture passes through the hole 113 for making the artificial dura 21 to be fixed under the partial skull 11.

Figure 10:
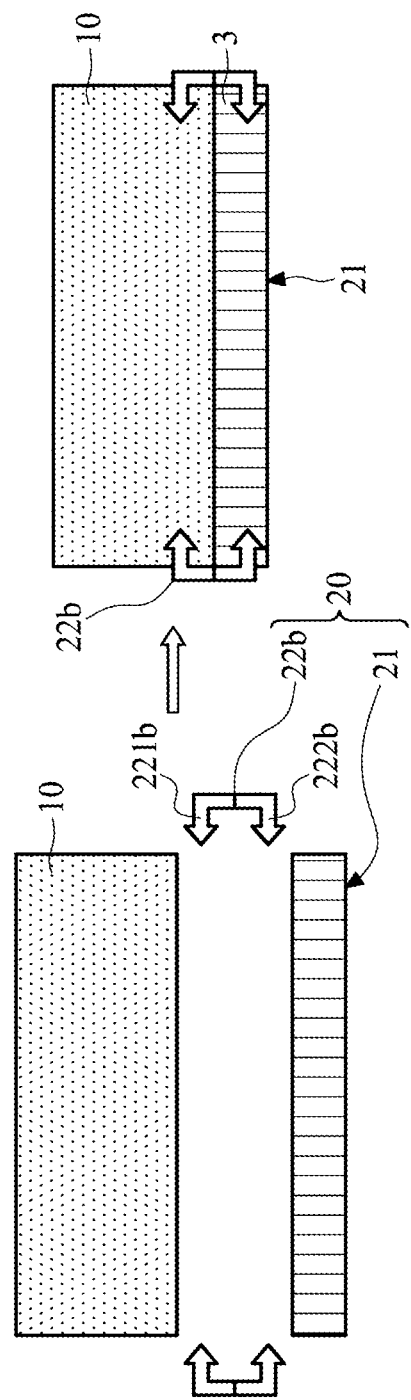
FIG. 10 is a schematic view showing a partial skull combined with an artificial dura biomedical device of another embodiment of the invention.
Figure 11:
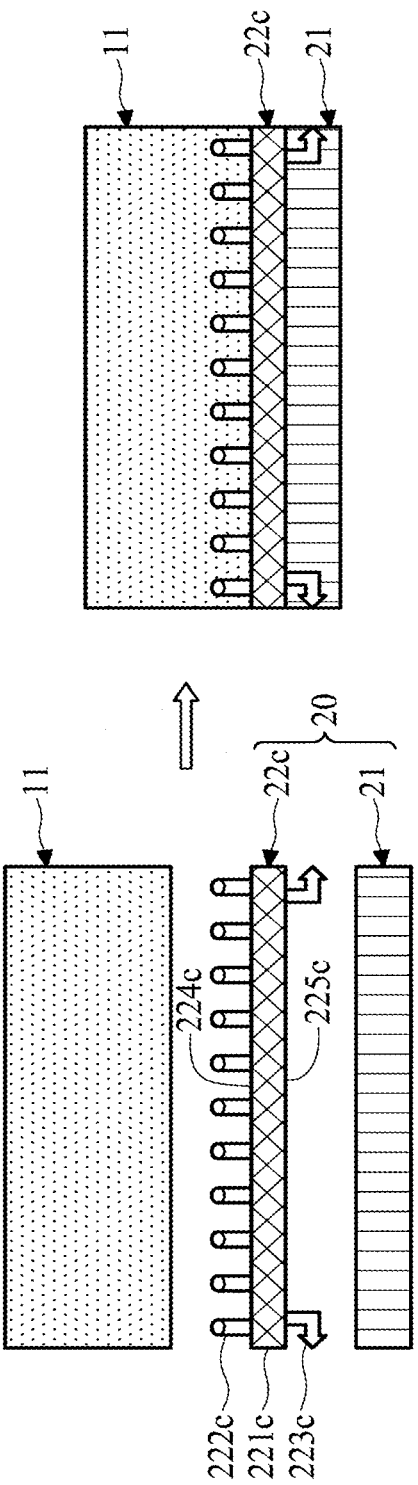
FIG. 11 is a schematic view showing a partial skull combined with an artificial dura biomedical device of another embodiment of the invention.

FIG. 10 is a schematic view showing a partial skull combined with an artificial dura biomedical device of another embodiment of the invention. FIG. 11 is a schematic view showing a partial skull combined with an artificial dura biomedical device of another embodiment of the invention.

Referring to FIG. 10, the connecting element 22b is installed between the partial skull 11 and the artificial dura 21. The connecting element 22b comprises two hook portions 221b and 222b respectively laterally inserted into the partial skull 11 and the artificial dura 21.

Referring to FIG. 11, the connecting element 22c comprises a base 221c, a first engaging portion 222c and a second engaging portion 223c. The first engaging portion 222c and the second engaging portion 223c are installed at two opposite surfaces 224c and 225c of the base 221c. The first engaging portion 222c is inserted into the partial skull 11, and the second engaging portion 223c is inserted into the artificial dura 21.

Figure 12:
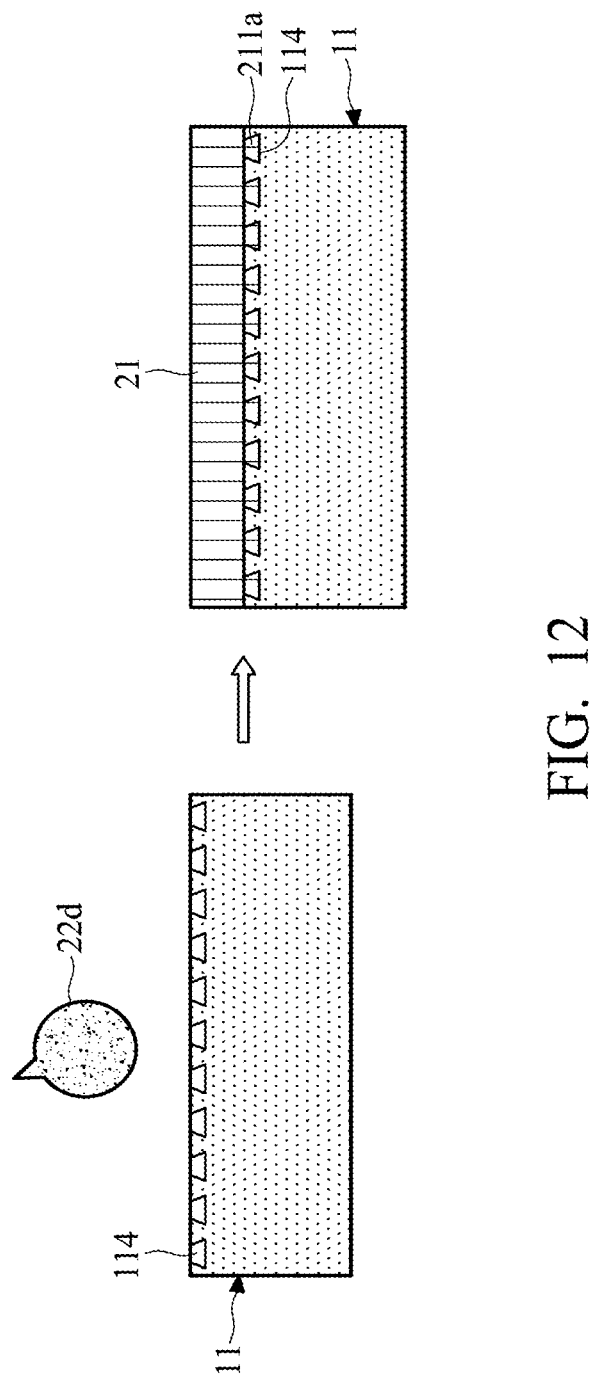
FIG. 12 is a schematic view showing a partial skull combined with an artificial dura biomedical device of another embodiment of the invention.

FIG. 12 is a schematic view showing a partial skull combined with an artificial dura biomedical device of another embodiment of the invention. Referring to FIG. 12, the partial skull 11 comprises a plurality of grooves 114. In this embodiment, the artificial dura 22d is liquid at an initial state. Thus, the liquid artificial dura 22d is poured on the partial skull 11 and fills the grooves 114. Due to the material feature, the liquid artificial dura 22d transforms into colloidal or solid artificial dura 21 and a plurality of protrusions 211a later. Thus, the artificial dura 21 is adhered on the partial skull 11 and is engaged with the partial skull 11 by the protrusions 211a. Note that the protrusions 211a and grooves 114 are wedge shaped. The artificial dura 22d at an initial state is liquid.

Figure 13:
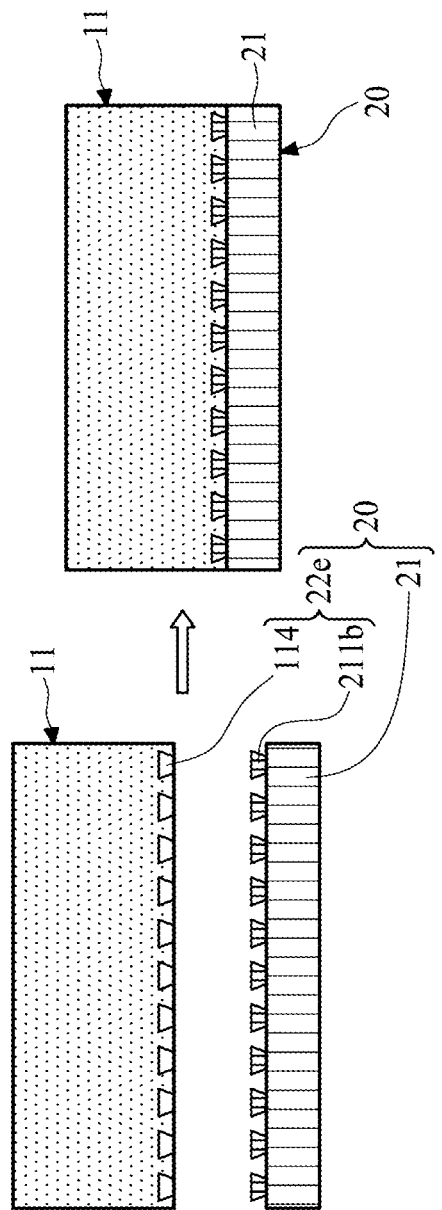
FIG. 13 is a schematic view showing a partial skull combined with an artificial dura biomedical device of another embodiment of the invention.

FIG. 13 is a schematic view showing a partial skull combined with an artificial dura biomedical device of another embodiment of the invention. The artificial dura biomedical device 20 comprises an artificial dura 21 and two connecting elements 22e. The connecting elements 22e comprise a plurality of protrusions 211b and grooves 114. The protrusions 211b are engaged with the grooves 114 for fixing the partial skull 11 to the artificial dura 21. In this embodiment, the protrusions 211b and the artificial dura 21 are a unitary and single member, and the grooves 114 are installed on the partial skull 11. Note that the protrusions 211b and grooves 114 are wedge shaped.

Figure 14:
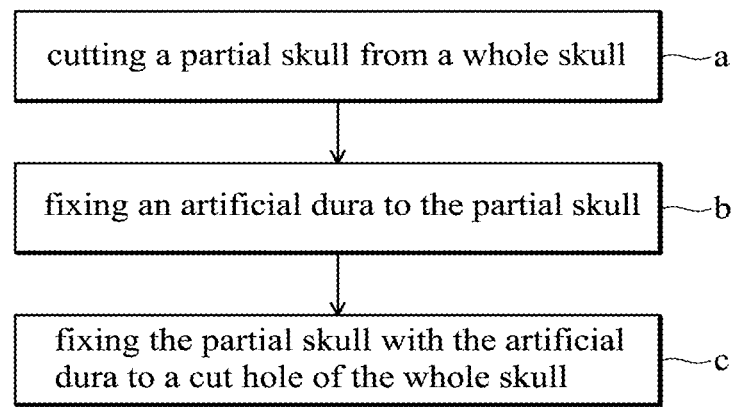
FIG. 14 is a flow chart showing a brain surgery method utilizing an artificial dura biomedical device of an embodiment of the invention.

FIG. 14 is a flow chart showing a brain surgery method utilizing an artificial dura biomedical device of an embodiment of the invention. Referring to FIGS. 1, 2 and 14, the steps comprises: a. cutting a partial skull 11 from a whole skull 10; b. fixing an artificial dura 21 to the partial skull 11; and c. fixing the partial skull 11 with the artificial dura 21 to a cut hole 12 of the whole skull 10. Note that the artificial dura 21 is cut as a suitable size and thickness in advance. In the b step, the artificial dura 21 may be fixed to the partial skull 11 via the connecting member 22a, 22b, 22c and 22e (shown in FIGS. 2-8, 10, 11 and 13). Alternatively, the artificial dura 21 may be fixed to the partial skull 11 via the protrusions 211a made of the liquid artificial dura 22d engaging with the grooves 114 of the partial skull 11 (shown in FIG. 12).

Figure 15:
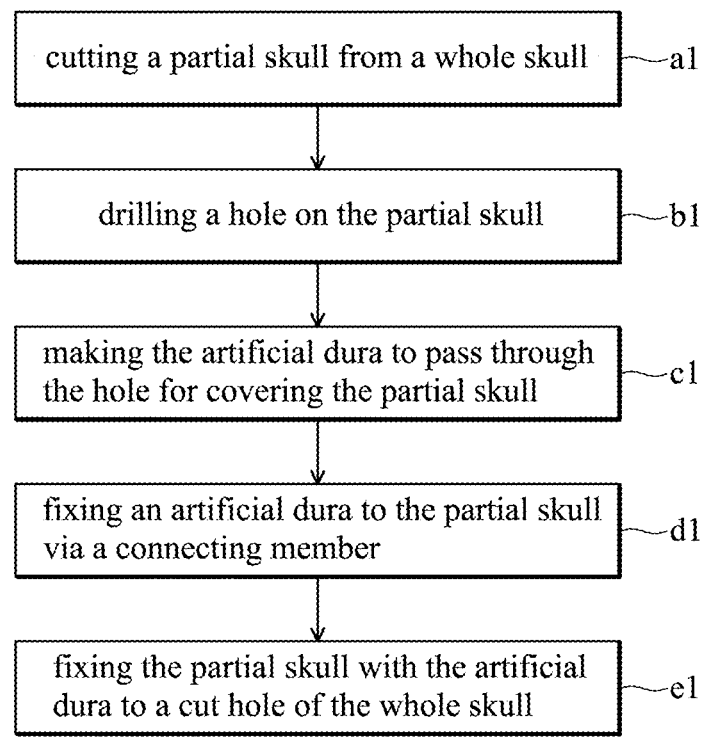
FIG. 15 is a flow chart showing a brain surgery method utilizing an artificial dura biomedical device of another embodiment of the invention.

FIG. 15 is a flow chart showing a brain surgery method utilizing an artificial dura biomedical device of another embodiment of the invention. Referring to FIGS. 1, 9 and 15, the steps comprises: a1. cutting a partial skull 11 from a whole skull 10; b1. drilling a hole 113 on the partial skull 11; c1. making the artificial dura 21 to pass through the hole 113 for covering the partial skull 11; d1. fixing an artificial dura 21 to the partial skull 11 via a connecting member 22; and e1. fixing the partial skull 11 with the artificial dura 21 to a cut hole 12 of the whole skull 10.

In summary, the invention avoids the artificial dura 21 from being directly sutured with the broken dura on the cerebral tissue to decrease risks and time-consumption of the brain surgery. Moreover, the artificial dura 21 fixed on the partial skull 11 can stably cover the broken dura via engagement of the whole skull 10 and eliminates movement in the whole skull 10 and leakage of cerebrospinal fluid.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A brain surgery method utilizing an artificial dura biomedical device, comprising:
    forming a cut hole in a whole skull of a patient by removing a partial skull therefrom;
    fixing an artificial dura to an entire interior surface of the partial skull; and
    fixing the partial skull with the artificial dura to the cut hole of the whole skull, such that the interior surface of the partial skull faces a brain of the patient.

2. The brain surgery method as claimed in claim 1, further comprising:
    drilling a hole on the partial skull.

3. The brain surgery method as claimed in claim 1, wherein the step of fixing the artificial dura to the partial skull comprises fixing the artificial dura to the partial skull via a plurality of protrusions made of a liquid artificial dura engaging with a plurality of grooves of the partial skull.

4. The brain surgery method as claimed in claim 1, wherein a step of performing a surgical procedure through the cut hole is performed after the step of forming the cut hole.

5. The brain surgery method as claimed in claim 1, wherein the partial skull is a single piece.

6. The brain surgery method as claimed in claim 1, wherein the step of fixing the artificial dura to the partial skull comprises fixing the artificial dura to the partial skull via a connecting member.

7. The brain surgery method as claimed in claim 6, wherein the connecting member comprises a screw, a hook, a rivet, glue, a suture, or a nail.

8. A brain surgery method utilizing an artificial dura biomedical device, comprising:
    forming a cut hole in a whole skull of a patient by removing a partial skull therefrom;
    performing a surgical procedure through the cut hole in which a dura of the patient is broken;
    fixing an artificial dura to an entire inner surface of the partial skull;
    fixing the partial skull with the artificial dura to the cut hole of the whole skull such that the broken dura is repaired by the artificial dura without directly suturing the artificial dura to cerebral tissue of the patient.

9. The brain surgery method as claimed in claim 8, wherein the step of fixing the artificial dura to the partial skull comprises fixing the artificial dura to the partial skull via a plurality of protrusions made of a liquid artificial dura engaging with a plurality of grooves of the partial skull.

10. The brain surgery method as claimed in claim 8, wherein the partial skull is a single piece.

11. The brain surgery method as claimed in claim 8, wherein the step of fixing the artificial dura to the partial skull comprises fixing the artificial dura to the partial skull via a connecting member.

12. The brain surgery method as claimed in claim 11, wherein the connecting member comprises a screw, a hook, a rivet, glue, a suture, or a nail.

\* \* \* \* \*